United States Patent [19]
Weissmann et al.

[11] Patent Number: 5,698,763

[45] Date of Patent: Dec. 16, 1997

[54] TRANSGENIC ANIMALS LACKING PRION PROTEINS

[76] Inventors: Charles Weissmann, Eschenhaustrasse 39, CH-8053 Zurich; Hansruedi Bueler, Riedweg 7, CH-8600 Dubendorf; Michel Aguet, Hadlaubstrasse 49, CH-8600 Zurich; Marek Fischer, Rothstrasse 19, CH-8057 Zurich; Andreas Sailer, Riedenhaldenstrasse 250, CH-8046 Zurich, all of Switzerland

[21] Appl. No.: 244,010

[22] PCT Filed: Nov. 26, 1992

[86] PCT No.: PCT/EP92/02631

§ 371 Date: Jun. 21, 1994

§ 102(e) Date: Jun. 21, 1994

[87] PCT Pub. No.: WO93/10227

PCT Pub. Date: May 27, 1993

[51] Int. Cl.[6] .............. C12N 15/00; C12N 5/00; C07H 21/04

[52] U.S. Cl. ............ 800/2; 536/23.1; 536/23.5; 435/172.3; 435/240.2; 800/DIG. 1

[58] Field of Search .............. 800/2; 536/24.5, 536/23.5, 23.1; 435/172.3, 514; 514/44

[56] References Cited

U.S. PATENT DOCUMENTS

| | | |
|---|---|---|
| 4,736,866 | 4/1988 | Leder et al. |
| 5,565,186 | 10/1996 | Prusiner .................. 424/92 |

FOREIGN PATENT DOCUMENTS

| | | | |
|---|---|---|---|
| 0351921 | 1/1990 | European Pat. Off. | A01K 67/00 |
| 0424027 | 4/1991 | European Pat. Off. | C12N 15/00 |
| 0424044 | 4/1991 | European Pat. Off. | C12N 15/00 |
| WO 8605516 | 9/1986 | WIPO | C12P 21/00 |
| WO 8808026 | 10/1988 | WIPO | C12N 15/00 |
| WO 9001541 | 2/1990 | WIPO | C12N 5/00 |
| WO 9101140 | 2/1991 | WIPO | A61K 37/00 |
| WO 9117174 | 11/1991 | WIPO | C07H 21/00 |

OTHER PUBLICATIONS

Haudebire, J. of Biotechnology 34:269, 1994.
Wale, Theriogenology 45:57, 1996.
Monsaur et al Nature 336:348, 1988.
Wesang et al Cell 51: 651, 1987.
Weissman Tetra 352: 679, 1991.
Uhlman et al Chemical Reviews 90(4):544, 1990.
A. Agrawal, "Antisense Oligonucleotides As Antiviral Agents", *Trends Biotech*, 10:152–158 (1992).
K. Basler et al., "Scrapie and Cellular PrP Isoforms are Encoded by the Same Chromosomal Gene", *Cell*, 46:417–28 (1986).
D.R. Borchelt et al., "Scrapie and Cellular Prion Proteins Differ in Their Kinetics of Synthesis and Topology in Cultured Cells", *J. Cell Biol.*, 110:743–52 (1990).
R.A. Bosselman et al., "Germline Transmission of Exogenous Genes in the Chicken", *Science*, 243:533–35 (1989).

A. Bradley, "Production and Analysis of Chimeric Mice", in Teratocarcinomas and Embryonic Stem Cells: A Practical Approach, (Robertson, ed.) Oxford IRL Press, pp. 113–151 (1987).
H. Büeler et al., "Normal Development And Behavior Of Mice Lacking The Neuronal Cell Surface PrP Protein", *Nature*, 356:577–82 (1992).
M.R. Capecchi, "Altering the Genome by Homologous Recombination", *Science*, 244:1288–92 (1989).
G.A. Carlson et al., "Primary Structure of Prion Protein May Modify Scrapie Isolate Properties", *Proc. Natl. Acad. Sci. USA*, 86:7475–79 (1989).
J.F. Case, Biology, 2nd ed., MacMillan Publishing Co., Inc., New York pp. 278–281 (1979).
N.R. Cashman et al., "Cellular Isoform of the Scrapie Agent Protein Participates in Lymphocyte Activation", *Cell*, 61:185–92 (1990).
B. Caughey et al., "Prion Protein Biosynthesis in Scrapie-Infected and Uninfected Neuroblastoma Cells", *J. Virol.*, 63:175–81 (1989).
C.A. Davis et al., "Expression of the Homeo Box–Containing Gene En–2 Delineates A Specific Region of the Developing Mouse Brain", *Genes Dev.*, 2:261–71 (1988).
J.R. Dorin et al., "Selection for Precise Chromosomal Targeting of a Dominant Marker by Homologous Recombination", *Science*, 243:1357–60 (1989).
K.M. Ebert et al., "Transgenic Production of a Variant of Human Tissue–Type Plasminogen Activator in Goat Milk: Generation of Transgenic Goats and Analysis of Expression", *Bio/Technology*, 9:835–38 (1991).
W. Goldmann et al., "Different Forms of the Bovine PrP Gene Have Five or Six Copies of a Short, G–C–Rich Element within the Protein–Coding Exon", *J. Gen. Virol.*, 72:201–04 (1991).
W. Goldmann et al., "Two Alleles of a Neural Protein Gene Linked to Scrapie in Sheep", *Proc. Natl. Acad. Sci. USA*, 87:2476–80 (1990).
L. Han et al., "Inhibition Of Moloney Murine Leukemia Virus–Induced Leukemia In Transgenic Mice Expressing Antisense RNA Complementary To The Retroviral Packaging Sequences" *Proc. Natl. Acad. Sci. USA*, 88:4314–17 (1991).
P. Hasty et al., "The Length of Homology Required for Gene Targeting in Embryonic Stem Cells", *Mol. Cell Biol.*, 11:5586–91 (1991).

(List continued on next page.)

*Primary Examiner*—Suzanne E. Ziska
*Attorney, Agent, or Firm*—Fish & Neave; James F. Haley, Jr.; Madge R. Kanter

[57] ABSTRACT

This invention relates to transgenic mammals and birds that are not susceptible to spongiform encephalopathies (i.e., scrapie-like or prion diseases), due to absence of endogenous functional prion protein ("PrP"). More particularly, this invention relates to DNA targeting molecules that specifically disrupt PrP genes by homologous recombination in transfected animal cells, to cultured cells transformed with such DNA targeting molecules, and to animals derived from those transformed cells and the transgenic progeny of such animals.

7 Claims, 5 Drawing Sheets

OTHER PUBLICATIONS

K.K. Hsiao et al., "Spontaneous Neurodegeneration in Transgenic Mice with Mutant Prion Protein", *Science*, 250:1587–90 (1990).

K. Hsiao and S.B. Prusiner, "Inherited Human Prion Diseases", *Neurology*, 40:1820–27 (1990).

K. Hsiao et al., "Linkage of a Prion Protein Missense Variant to Gerstmann–Straussler Syndrome", *Nature*, 338:342–45 (1989).

N. Hunter et al., "Linkage of the Scrapie–Associated Fibril Protein (PrP) Gene and Sinc Using Congenic Mice and Restriction Fragment Length Polymorphism Analysis", *J. Gen. Virol.*, 68:2711–16 (1987).

M. Jasin and P. Berg, "Homologous Integration in Mammalian Cells Without Target Gene Selection", *Genes Dev.*, 2:1353–63 (1988).

A.L. Joyner et al., "Production of a Mutation in Mouse En–2 Gene by Homologous Recombination in Embryonic Stem Cells", *Nature*, 338:153–56 (1989).

P. Krimpenfort et al., "Generation of Transgenic Dairy Cattle Using 'In Vitro' Embryo Production", *Bio/Technology*, 9:44–47 (1991).

F.L. Lin et al., "Homologous Recombination in Mouse L Cells", *Cold Spring Harbor Symposia on Quantitative Biology*, vol. XLIX, pp. 139–149 (1984).

R.M. Liskay et al., "Homology Requirement for Efficient Gene Conversion Between Duplicated Chromosomal Sequences in Mammalian Cells", *Genetics*, 115:161–67 (1987).

D. Lo et al., "Expression of Mouse IgA by Transgenic Mice, Pigs and Sheep", *Eur. J. Immunol.*, 21:1001–06 (1991).

C. Locht et al., "Molecular Cloning and Complete Sequence of Prion Protein cDNA from Mouse Brain Infected with the Scrapie Agent", *Proc. Nat. Acad. Sci. USA*, 83:6372–76 (1986).

J. Manson et al., "The Prion Protein Gene: A Role In Mouse Embryogenesis?", *Development*, 115:117–22 (1992).

S.L. Mansour et al., "Disruption of the Proto–Oncogene int–2 in Mouse Embryo–Derived Stem Cells: A General Strategy for Targeting Mutations to Non–Selectable Genes", *Nature*, 336:348–52 (1988).

A.P. McMahon and A. Bradley, "The Wnt–1 (int–1) Proto–Oncogene is Required for Development of a Large Region of the Mouse Brain", *Cell*, 62:1073–85 (1990).

B. Oesch et al., "A Cellular Gene Encodes Scrapie PrP 27–30 Protein", *Cell*, 40:735–46 (1985).

S.B. Prusiner, "Molecular Biology of Prion Diseases", *Science*, 252:1515–22 (1991).

V.G. Pursel et al., "Genetic Engineering of Livestock", *Science*, 244:1281–88 (1989).

R.E. Race et al., "Analysis of Linkage Between Scrapie Incubation Period and the Prion Protein Gene in Mice", *J. Gen. Virol.*, 71:493–97 (1990).

C.E. Rexroad et al., "Production of Transgenic Sheep with Growth–Regulating Genes", *Mol. Reprod. Dev.*, 1:164–69 (1989).

N.K. Robakis et al., "Isolation Of A cDNA Clone Encoding The Leader Peptide Of Prion Protein And Expression Of The Homologous Gene In Various Tissues" *Proc. Natl. Acad. Sci.*, USA, 83:6377–81 (1986).

M. Rothenberg et al., "Oligonucleotides As Anti–Sense Inhibitors Of Gene Expression: Therapeutic Implications", *J. Natl. Cancer Inst.*, 81:1539–45 (1989).

D.W. Salter et al., "Transgenic Chickens: Insertion of Retroviral Genes into the Chicken Germ Lines", *Virology*, 157:236–40 (1987).

M. Scott et al., "Transgenic Mice Expressing Hamster Prion Protein Produce Species–Specific Scrapie Infectivity and Amyloid Plaques", *Cell*, 59:847–57 (1989).

J.M. Sedivy and P.A. Sharp, "Positive Genetic Selection for Gene Disruption in Mammalian Cells by Homologous Recombination", *Proc. Natl. Acad. Sci., USA*, 86:227–31 (1989).

K.R. Thomas and M.R. Capecchi, "Site–Directed Mutagenesis by Gene Targeting in Mouse Embryo–Derived Stem Cells", *Cell*, 51:503–12 (1987).

C. Weissmann, "A 'Unified Theory' of Prion Propagation", *Nature*, 352:679–83 (1991).

D. Westaway et al., "Unraveling Prion Diseases Through Molecular Genetics", *Trends Neurol. Sci.*, 6:221–27 (1989).

D. Westaway et al., "Paradoxical Shortening of Scrapie Incubation Times by Expression of Prion Protein Transgenes Derived from Long Incubation Period Mice", *Neuron*, 7:59–68 (1991).

R.P. Woychik et al., "An Inherited Limb Deformity Created By Insertinal Mutagenesis In A Transgenic Mouse", *Nature*, 318:36–40 (1985).

G. Wright et al., "High Level Expression of Active Human Alpha1–Antitrypsin in the Milk of Transgenic Sheep", *Bio/Technology*, 9:830–34 (1991).

A. Zimmer and P. Gruss, "Production of Chimaeric Mice Containing Embryonic Stem (ES) Cells Carrying a Homeobox Box 1.1 Allele Mutated by Homologous Recombination", *Nature*, 338:150–52 (1989).

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

GCTTTCTTCA AGTCCTTGCT CCTGCTGTAG    30

( 2 ) INFORMATION FOR SEQ ID NO:2:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

TGACTCGAGG GTTCGCCATG ATGACT    26

( 2 ) INFORMATION FOR SEQ ID NO:3:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

ATTCGCAGCG CATCGCCTTC TATCGCC    27

( 2 ) INFORMATION FOR SEQ ID NO:4:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

CCTGGGAATG AACAAAGGTT TGCTTTCAAC    30

( 2 ) INFORMATION FOR SEQ ID NO:5:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:5:

GTACCCATAA TCAGTGGAAC AAGCCCAGC    29

TRANSGENIC ANIMALS LACKING PRION PROTEINS

TECHNICAL FIELD OF THE INVENTION

This invention relates to transgenic mammals and birds ("animals") that are not susceptible to spongiform encephalopathies (i.e., scrapie-like or prion diseases), due to absence of endogenous prion protein ("PrP"). More particularly, this invention relates to targeting molecules that are capable of disrupting PrP genes, PrP genes that are disrupted by such targeting molecules and thus incapable of expressing functional prion protein, to cultured cells transformed to have such disrupted genes, to mammals and birds derived from those transformed cells and to the transgenic progeny of such animals.

BACKGROUND OF THE INVENTION

Prions are infectious pathogens that cause spongiform encephalopathies in humans and animals. Prions are distinct from bacteria, viruses and viroids. The predominant hypothesis at present is that no nucleic acid component is necessary for infectivity of prion protein.

Kuru, Creutzfeldt-Jakob disease ("CJD") and Gerstmann-Sträussler-Scheinker syndrome ("GSS") are fatal human neurodegenerative diseases caused by prions. Scrapie of sheep and goats is the most well-studied prion disease. Bovine spongiform encephalopathy ("BSE" or "mad cow disease") is a prion disease that currently threatens the beef industry in Great Britain. Transmissible mink encephalopathy and chronic wasting disease of deer and elk are also thought to be prion diseases. The pathological characteristics of prion diseases include neuronal vacuolation, astrocytic gliosis, and amyloid plaques with filaments composed of prion protein.

A major step in the study of prions and the diseases that they cause was the discovery and purification of a protein designated prion protein ("PrP") (Bolton et al., Science 218, pp. 1309–11 (1982); Prusiner et al., Biochemistry 21, pp. 6942–50 (1982); McKinley et al., Cell 35, pp. 57–62 (1983)). Complete prion protein-encoding genes have since been cloned, sequenced and expressed in transgenic animals. $PrP^C$ is encoded by a single-copy host gene (Basler et al., Cell 46, pp. 417–28 (1986)) and is normally found at the outer surface of neurons. A leading hypothesis is that prion diseases result from conversion of $PrP^C$ into a modified form called $PrP^{Sc}$.

The actual biological or physiological function of $PrP^C$ is not known. Suggestions that it is identical with acetylcholine receptor inducing activity ("ARIA") remain to be confirmed (Harris et al., Proc. Natl. Acad. Sci. USA 88, pp. 7664–68 (1991)). The PrP gene, however, is found in all mammals so far examined, i.e., hamster (Basler et al., Cell 46, pp. 417–28 (1986)), mouse (Locht et al., Proc. Natl. Acad. Sci. USA 83, pp. 6372–76 (1986)), human (Kretzschmar et al., DNA 5, pp. 315–24 (1986); Puckett et al., Am. J. Hum. Genet. 49, 320–29 (1991)), rat (Westaway and Prusiner, Nucl. Acids Res. 14, 2035–44 (1986)), cattle (Goldmann et al., J. Gen. Virol. 72 pp. 201–04 (1991)), sheep (Goldmann et al., Proc. Natl. Acad. Sci USA 87, pp. 2476–80 (1990)), and goat (Westaway and Prusiner, supra). The PrP gene is also found in chickens (Harris et al., Proc. Natl. Acad. Sci. USA 88, pp. 7664–68 (1991)). Furthermore, because $PrP^C$ is expressed in neurons of the brain (Kretzschmar et al., Am. J. Pathol. 122, pp. 1–5 (1986)) as well as in lymphocytes (Cashman et al., Cell 61, pp. 185–92 (1990)) and shows a high turnover rate (Caughey et al., J. Virol 63, pp. 175–81 (1989); Borchelt et al., J. Cell. Biol. 110, pp. 743–52 (1990)), it would seem to be of considerable physiological importance.

The central role of $PrP^C$ in scrapie-like diseases is indicated by several lines of evidence. The infectious agent copurifies with $PrP^{Sc}$ by different procedures (Prusiner, Science 216, pp. 136–44 (1982); Diringer et al., Nature 306, pp. 476–78 (1983); McKinley et al., Cell 35, pp. 57–62 (1983); Hope et al., EMBO J. 5, pp. 2591–97 (1986)), including affinity purification on an anti-PrP antibody column (Gabizon et al., Proc. Natl. Acad. Sci. USA 85, pp. 6617–21 (1988)), SDS-polyacrylamide gel electrophoresis (Brown et al., Proc. Natl. Acad. Sci. USA 87, pp. 7240–44 (1990)) and HPLC (Safar et al., Proc. Natl. Acad. Sci. USA 87, pp. 6373–77 (1990)). Further, the susceptibility of a host to scrapie is determined, at least in part, by the nature of its Prn-p alleles (Dickinson et al., J. Comp. Pathol. 78, pp. 293–99 (1968); Dickinson and Meikle, Mol. Gen. Genet. 112, pp. 73–79 (1971); Carlson et al., Cell 46, pp. 503–11 (1986); Hunter et al., J. Gen. Virol. 68, pp. 2711–16 (1987); Carlson et al., Proc. Natl. Acad. Aci USA 86, pp. 7475–79 (1989); Race et al., J. Gen. Virol. 71, pp. 493–97 (1990); Westaway et al., Neuron 7, pp. 59–68 (1991)). Finally, certain mutations in the PrP gene, such as a proline to leucine change in position 102, are tightly linked to morbidity in some familial forms of spongiform encephalopathies (Hsiao et al., Nature 338, pp. 342–45 (1989); Hsiao and Prusiner, Neurology 40, pp. 1820–27 (1990)). Furthermore, mice carrying a PrP transgene with the analogous amino acid change succumb to a spontaneous scrapie-like disease (Hsiao et al., Science 250, pp. 1587–90 (1990)). However, to date there has been no way to prevent the disease.

SUMMARY OF THE INVENTION

This invention solves the above problem. It relates to mammals and birds lacking functional PrP genes, and thus devoid of prion proteins. Those transgenic animals not only survive and develop normally, but they are not susceptible to prion diseases. More particularly, this invention relates to PrP genes that are disrupted and thus incapable of expressing prion protein, to PrP antisense genes, to cultured cells transformed with such disrupted genes or antisense genes, and to mammals and birds derived from those transformed cells and to transgenic progeny of such animals. This invention also relates to therapeutic administration of antisense oligonucleotides to non-transgenic animals and humans who have an incipient spongiform encephalopathy.

DETAILED DESCRIPTION OF THE INVENTION

Figure 1:
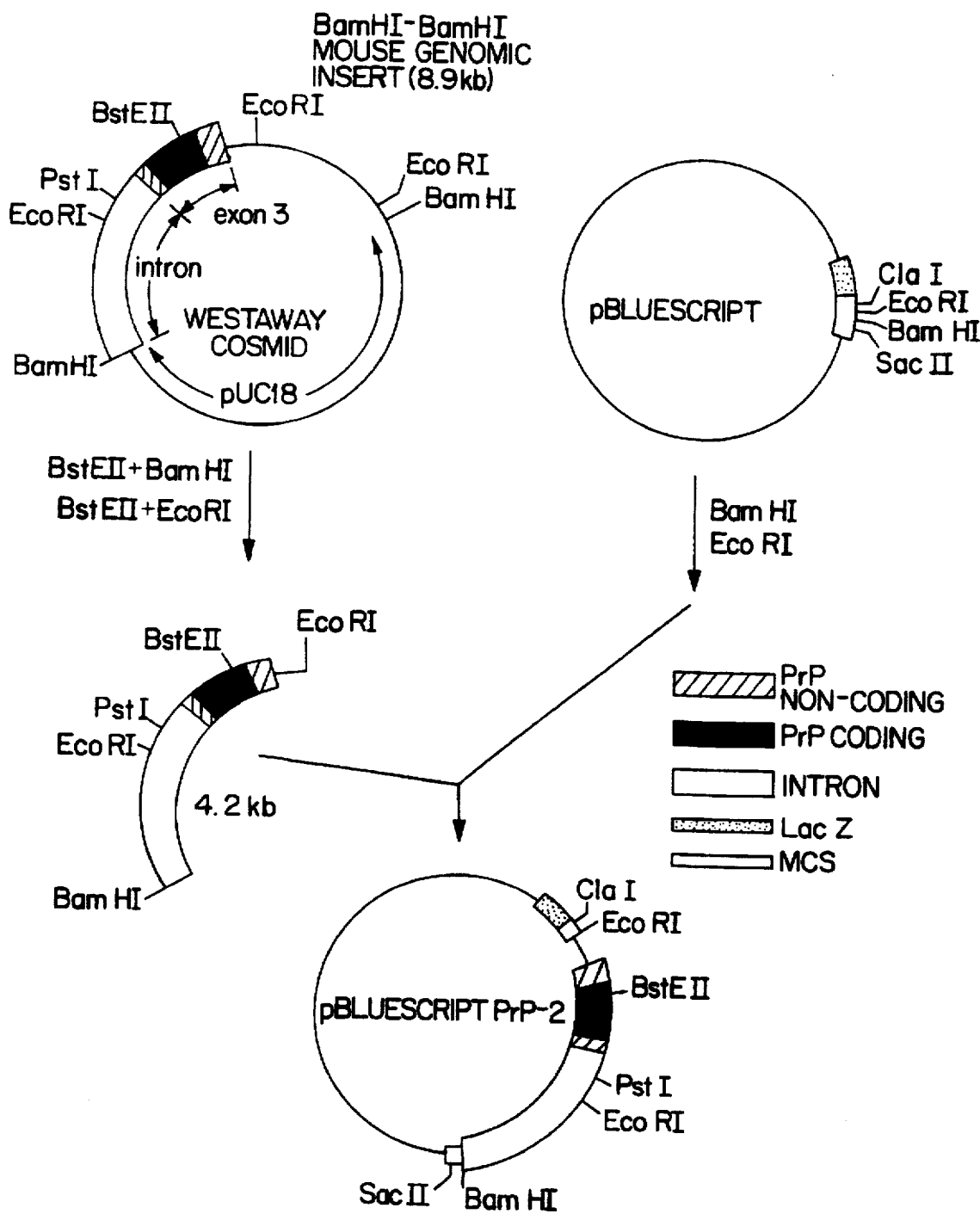
FIG. 1 depicts construction of plasmid pBluescriptPrP-2 from the Westaway cosmid and plasmid pBluescript.

In the description of the present invention, the following terms are employed:

Critical site—Site (or sites) within a PrP gene that is required for expression of functional prion protein.

Disrupting sequence—Nucleotide sequence in a targeting molecule that disrupts a target gene upon site-specific integration of the targeting molecule so as to prevent expression of functional PrP protein.

ES cells—Embryonic stem cells.

Expression control sequence—Sequence of nucleotides that enables and regulates transcription of a nucleotide sequence when operatively linked to that sequence.

Homologous recombination—Rearrangement of DNA segments at a sequence-specific site (or sites) within or between DNA molecules through base-pairing mechanisms.

Homologous region—Sequence within the target gene locus chosen for duplication in the targeting molecule, having sufficient length and homology to provide for site-specific integration of the targeting molecule into the target gene locus by homologous recombination.

PCR—Polymerase chain reaction.

PrP—Prion protein.

Prn-p—Gene encoding prion protein.

Target gene locus—Chromosomal site of target gene, including the PrP coding sequence, PrP expression control sequences, PrP 3' untranslated sequences, and 5' and 3' PrP gene-neighboring regions on the chromosome.

Targeting fragment—Targeting molecule consisting of fragment from targeting plasmid.

Targeting molecule—DNA molecule, linear or circular, capable of specifically disrupting a PrP target gene in a transfected cell by homologous recombination so as to prevent expression of functional PrP protein.

Targeting plasmid—Intermediate in construction of targeting fragment.

The first step in producing the transgenic animals of this invention is to prepare a DNA sequence ("targeting molecule") that is capable of specifically disrupting a PrP gene in animal cells carrying that gene and rendering that gene non-functional. The targeting molecule is then used to transfect animal cells and to disrupt the functional PrP genes in those cells. The transgenic animal cells may then be used to produce the transgenic mammals and birds of this invention.

DNA targeting molecules that are capable, in accordance with this invention, of disrupting a functional PrP gene resident in cells may be produced using information and processes well known in the art.

Any DNA targeting molecule of the present invention has two essential functions. Those essential functions are to integrate at a native resident PrP gene ("target gene locus") and to disrupt PrP gene expression associated with that locus so that no functional PrP expression is possible. Those two essential functions depend on two basic structural features of the targeting molecule.

The first basic structural feature of the targeting molecule is a pair of regions that are homologous to chosen regions of the target gene locus. That homology (in terms of both sequence identity and length) causes the targeting molecule to integrate by base pairing mechanisms ("homologous recombination") at the site chosen in the target gene locus in transfected cells.

Homologous recombination is the rearrangement of DNA segments at a sequence-specific site (or sites) within or between DNA molecules through base-pairing mechanisms. The present invention relates to a particular form of homologous recombination sometimes called "gene targeting". In gene targeting, an exogenous "targeting molecule" (or "targeting fragment") is introduced into cells. The targeting molecule has one or more regions of homology with a chromosomal gene to be modified or replaced ("target gene"). The regions of homology between the target gene and the targeting molecule result in site-specific integration of the exogenous sequence. Of course, the exogenous sequence may be designed to correct an existing defect in the resident gene or to disable ("disrupt") a functional resident gene. The present invention relates to disrupting PrP genes. Gene targeting, which affects the structure of a specific gene already in a cell, is to be distinguished from other forms of stable transformation wherein integration of foreign DNA for expression is not site-specific, and thus does not predictably affect the structure of any particular gene already in the cell.

The second basic structural feature of the targeting molecule of this invention is a disrupting sequence between the homologous regions. The disrupting sequence prevents expression of functional prion protein from the PrP target gene following the replacement of a portion of that target gene by the integrated targeting molecule.

One of skill in the art will recognize that numerous embodiments of the PrP gene targeting molecule of the present invention may be constructed to fulfill the structural and functional requirements specified above. Example 1 (below) describes the actual construction of a PrP gene targeting molecule used to produce the transgenic mice of the present invention. The following discussion sets forth considerations and parameters that can be used to design other PrP gene targeting molecules that may be used to produce transgenic mice, hamsters, rabbits, sheep, pigs, cattle, chickens and other mammals and birds without departing from the scope of the present invention.

Parameters of the targeting molecule that may be varied in the practice of the present invention include the lengths of the homologous regions, what regions of the target gene locus are to be duplicated as the homologous regions of the targeting molecule, the length of the disrupting sequence, the identity of the disrupting sequence, and what sequence of the target gene is to be replaced by the targeting molecule.

The length of the homologous regions that flank the disrupting sequence of the targeting molecules of this invention can vary considerably without significant effect on practice of the invention. The homologous flanking regions must be of sufficient length for effective heteroduplex formation between one strand of the targeting molecule and one strand of a transfected cell's chromosome, at the PrP target gene locus. Increasing the length of the homologous regions promotes heteroduplex formation and thus targeting efficiency. However, it will be appreciated that the incremental targeting efficiency accruing per additional homologous base pair eventually diminishes and is offset by practical difficulties in targeting molecule construction, as homologous regions exceed several thousand base pairs. A preferred range for the length of each homologous region is 50 to 5,000 base pairs, and about 500 base pairs is most preferred. It should be further noted that the precise length of the homologous regions in the DNA targeting molecule may depend in practice on the location of restriction sites in and around the PrP gene. For a discussion of the length of homology required for gene targeting in embryonic stem cells, see Hasty et al. (*Mol. Cell Biol.* 11, 5586–91 (1991)).

There is considerable latitude in choice of which regions of the target gene locus are duplicated as the homologous regions in the targeting molecule. The basic constraints are that the PrP target gene sequence to be replaced by the disrupting region must lie between the regions of the target gene locus duplicated as the homologous regions in the targeting molecule, and that replacement of the target gene sequence must render the PrP gene non-functional. It should be noted that the target gene locus nucleotide sequences chosen for homology in the targeting molecule remain unchanged after integration of the targeting molecule. Those sequences of the target gene locus are merely replaced by the duplicate (homologous) sequences in the targeting molecule. Identity between the chosen regions of the target gene locus and the homologous regions in the targeting molecule is the means by which the targeting molecule delivers the disrupting sequence precisely into the PrP target gene. The chosen regions of homology may lie within the PrP coding sequence, but it is not necessary that they do so. For example, in an embodiment of the present invention, one homologous region could be located 5' from the PrP gene, and the other homologous region could be located 3' from the PrP gene. Preferably, the PrP initiation codon and 5' terminal region of the PrP coding sequence will lie between the chosen homologous regions and thus be replaced by the interrupting sequence, so that no portion of the prion protein can be expressed. Even more preferred, when the interrupting sequence contains a selectable marker (or any other gene), is that there is a termination codon downstream of the minimum required marker coding sequence, and in-frame with the marker coding sequence, to prevent translational read-through that might yield a PrP fusion protein with PrP activity. As a practical matter, other than the requirement that some critical site of the PrP gene lie between the homologous regions (so that it will be disrupted), the primary constraints on choice of homologous regions is the availability of the cloned sequences and the existence of restriction sites therein. Preferably, the regions chosen to be homologous regions will not include sequences longer than about 20 nucleotides that are known to occur elsewhere in the genome being modified. Extensive homology between the targeting molecule and other (non-target) sites in the genome might diminish targeting efficiency by diverting targeting molecules into non-productive heteroduplexes at non-target sites.

The length of the disrupting sequence separating the homologous regions in the targeting molecule can also vary considerably without significant effect on the practice of the present invention. The minimum length of the disrupting sequence is one base pair. Insertion of a single base pair in the PrP coding sequence would constitute a frame shift mutation and thus could prevent expression of a functional prion protein. Alternatively, a single base pair substitution could result in an amino acid substitution at a critical site in the prion protein and the expression of only non-functional prion protein. It should be recognized, however, that a single base pair alteration is susceptible to reversion to the wild type sequence through spontaneous mutation. For that reason, disrupting sequences longer than one base pair are preferred. At the other extreme, excessive length in the disrupting sequence would be unlikely to confer any advantage over a disrupting sequence of moderate length, and might diminish efficiency of transfection or targeting. Excessive length in this context is many times longer than the distance between the chosen homologous regions on the target gene. A preferred length for the disrupting sequence is from 2 to 2,000 base pairs. A more preferred length for the disrupting sequence is a length approximately equivalent to the distance between the regions of the target gene locus that match the homologous regions in the targeting molecule.

There is wide latitude in the choice of the of the disrupting sequence, since the disrupting function is not sequence-specific. It is necessary, however, that the nucleotide sequence of the disrupting region not express a functional prion protein and not express a protein or polypeptide toxic to the transformed cell. It is also preferred that the disrupting sequence not be extensively homologous to sites in the genome of the transfected cell. Such homology would be likely to diminish the efficiency of the targeting molecule, and might severely impair its function.

For some embodiments of the present invention it is preferred that the disrupting sequence have a dual function, i.e., be both a selectable marker and a disrupting sequence. In those embodiments, the length and identity of the disrupting sequence will be determined largely by the selectable marker coding sequence and associated expression control sequences. The selectable marker gene provides for positive selection of transfected cells that have taken up and integrated the targeting molecule. The need for a selectable marker will depend on the methods chosen for transfection of cells and transgenic animal production. The choice of those methods, in turn, will depend on the species of animal on which this invention is being practiced. For example, a preferred method for production of transgenic birds (described below) does not comprise a selectable marker. In another example (Examples 1 and 2 below), a preferred method for production of transgenic mice involves murine ES cells, and a preferred method of transfecting ES cells is electroporation, with which a selectable marker is preferred. The preferred selectable marker is the antibiotic resistance gene, neomycin phosphotransferase ("neo"). A neo gene with mammalian expression control sequences is commercially available (Stratagene Cloning Systems, La Jolla, Calif.). Although neo is preferred for mammalian cell selection, other marker genes, such as thymidine kinase, dihydrofolate reductase, hygromycin B phosphotransferase, xanthine-guanine phosphoribosyl transferase, adenosine deaminase, asparagine synthetase and CAD (carbamyl phosphate synthetase/aspartate transcarbamylase/dihydroorotase) may be used with appropriate culture media.

In plasmid pRVPrP3, the targeting plasmid of the present invention described in Example 1 below and FIGS. 1–5, 72% (codons 4 to 187) of the PrP coding sequence was replaced with a fragment containing a neo gene under the control of the HSV TK promoter (Thomas and Capecchi, *Cell* 51, pp. 503–12 (1987)).

In this discussion, the targeting molecule is described as a linear DNA molecule. However, it should be recognized that a targeting molecule of the present invention could also be embodied as a circular DNA molecule. A circular targeting molecule could comprise a pair of homologous regions separated by a disrupting region, as described for a linear targeting molecule. Alternatively, a circular targeting molecule could comprise a single homologous region. Upon integration at the target gene locus, the circular molecule would become linearized, with a portion of the homologous region at each end. Thus, the single homologous region effectively becomes two homologous regions, as described in the discussion of linear targeting molecules (see Watson et al., *Molecular Biology of the Gene* (4th Ed.), Benjamin/Cummings, Menlo Park, Calif., p. 606). One differing aspect of a circular targeting molecule with a single homologous region is that it inserts the disrupting sequence into the target gene and disrupts it without replacing any of the target gene. A second differing aspect is that the single homologous region must be within the target gene and located 5' to at least one critical site in the PrP coding sequence.

The foregoing discussion focuses on PrP gene disruption by homologous recombination, for production of transgenic animals devoid of prion protein—the preferred embodiment. However, in another embodiment the present invention also provides heterozygous animals having one gene encoding prion protein. Such animals are at least partially protected against scrapie. They produce prion protein, but at a lowered level, due to a gene dosage effect. (Wild type animals have two prion genes.) And this lowered prion protein level confers significant resistance against spongiform encephalopathy.

Lowering of prion protein levels, without PrP gene disruption, is thus an alternative means, in accordance with this invention, of producing resistance to spongiform encephalopathy. One of skill in the art can, for example, advantageously reduce prion protein levels by application of well known antisense techniques. Antisense techniques, for example, may be applied in either of two different approaches. The first antisense approach is production of transgenic animals whose cells transcribe prion antisense sequences. The second antisense approach is therapeutic administration of antisense oligonucleotides to non-transgenic animals and humans who have an incipient spongiform encephalopathy.

Ribozymes are RNA molecules with endoribonuclease activity. Ribozyme sequences may be combined with anti-sense sequences to specifically inhibit production of a particular protein. In an additional emobidment of this invention, one of ordinary skill in the art can advantageously reduce prion protein levels by linking ribozyme sequences to prion antisense sequences, thereby targeting the endoribonuclease activity specifically to the prion mRNA, to inhibit biosynthesis of prion protein. Such a prion antisense-ribozyme RNA molecule may by provided indirectly by transcription of a recombinant DNA construct in the cells of transgenic animals. Alternatively, such a prion antisense-ribozyme RNA molecule may be provided directly by therapeutic administration of the RNA molecule to non-transgenic animals or humans. For a general discussion of ribozyme technology, see, inter alia: Cech, "Ribozymes and Their Medical Implications", *J. American Medical Association*, vol. 260, pp. 3030–34 (1988); Haseloff and Gerlach, "Simple RNA Enzymes with New and Highly Specific Endoribonuclease Activities", *Nature*, vol. 334, pp. 585–91 (1988).

It should be recognized from the foregoing discussion that practice of the present invention requires a DNA clone comprising at least a portion of the PrP target gene or DNA clones comprising sequences between which at least a portion of the PrP target gene lies. Such DNA clones necessary for practice of the present invention may be obtained by a variety of means. Mouse (Locht et al. *Proc. Natl. Acad. Sci. USA*, 83, pp. 6372–76 (1986)), hamster (Basler et al., *Cell*, 46, pp. 417–28 (1986)), sheep (Goldmann et al., *Proc. Natl. Acad. Sci. USA* 87, pp. 2476–80 (1990)), cow (Goldmann et al., *J. Gen. Virol.* 72, pp. 201–04 (1991)) and human (Kretzschmar et al., *DNA* 5, pp. 315–24 (1986)) PrP genes have been cloned and sequenced. DNA clones suitable for practice of the present invention on those species may be obtained by following the PrP gene cloning methods set forth in the publications cited above, by use of the sequences published therein for chemical synthesis of PrP genes or portions thereof, or by use of the published sequences for chemical synthesis of oligonucleotide probes which may be used in well-known procedures to isolate PrP gene sequences from a cDNA library or a genomic library. The published nucleotide sequence of a PrP gene from one species, can be used to obtain a PrP gene from another species, without undue experimentation, because the nucleotide sequences of all known PrP coding regions are highly conserved (80%–90% identical). In addition, even the 3' untranslated regions are conserved in hamsters, sheep and humans. The use of a PrP gene sequence from one sequence to isolate a PrP gene from a different species has been demonstrated by Goldmann et al. (supra), who isolated a sheep PrP gene by screening a sheep genomic library with a hamster PrP cDNA.

The preferred method of obtaining a cloned PrP gene sequence is:

(a) using published PrP gene sequence data to synthesize oligonucleotide primers (representing the ends of the desired DNA fragment), using known techniques, and (b) using the primers prepared in (a) in known PCR procedures, wherein DNA from the animal species of interest serves as the template.

DNA targeting molecules constructed to disrupt PrP genes according to the present invention may be used to transfect animal cells using well known techniques. Such transfection results in the DNA sequences of this invention disrupting the functional PrP genes in those animal cells. The cell type chosen for transfection with the PrP targeting molecule must be pluripotent. The defining characteristic of pluripotent cells is developmental plasticity, which is necessary for production of a transgenic animal. Pluripotent cells are exemplified by oocytes, sperm and embryonic cells. Oocytes and embryonic cells are preferred in the practice of the present invention. Animal species is a major factor in the choice of pluripotent cell type to be used in practicing the present invention. For example, ES cell culture methods are not fully developed for all species.

Single-cell embryos (also called zygotes) are preferred for transfection and production of transgenic mammals such as pigs, sheep and cattle. Single cell embryos are either obtained surgically or produced by in vitro fertilization. Embryonic stem cells maintained in culture are preferred for the production of transgenic small mammals such as mice and hamsters. Embryonic cells of a newly laid egg are preferred for production of transgenic birds such as chickens.

The method of Krimpenfort et al. (*Bio/Technology* 9, pp. 844–47 (1991)) is preferred for production of transgenic cattle and other large mammals in accord with the present invention. In that method, immature oocytes are collected by aspiration of follicles on ovaries from slaughtered animals. The oocytes are fertilized in vitro by standard techniques. The DNA targeting molecule is placed in the pronucleus of the single-cell embryo by microinjection at an appropriate time interval after oocyte fertilization (between 16 and 23 hours for cattle). Differential interference contrast microscopy is preferred for microinjection of bovine zygotes, due to their opacity. The embryos are cultured for an appropriate period following microinjection (nine days for cattle), and they are then evaluated for development and normal appearance. An animal that started estrous on the same day that the oocytes were fertilized is used as a recipient of one or two cultured embryos that have developed to the compact morula or early blastula stage.

In an alternative microinjection approach for producing transgenic mammals, including sheep and cattle, early embryos are obtained surgically from oviducts of superovulated, artificially inseminated mammals, subjected to microinjection of the PrP targeting molecule, and transferred back to the donor female or another physiologically receptive female for gestation (Ebert et al., *Bio/Technology*

9, pp. 835–38. (1991)). The use of embryos retrieved after in vivo fertilization may yield a somewhat higher number of transgenic animals per embryo, but the method is more labor-intensive than the method of Krimpenfort et al., described above. For a discussion of surgical techniques used to obtain single-cell embryos from sheep, see PCT patent publication WO 90/08832.

ES cell culture can be used to produce transgenic animals of the present invention without microinjection. For a discussion of the culturing of ES cells and their use in the production of transgenic animals, see PCT patent publication WO 90/0154. ES cells are preferred for the production of small transgenic mammals with short generation intervals and large litter size. Generation interval and litter size are factors to be considered, because the ES cell method yields chimeric animals. Advantages of the ES cell method are that ES cells can be maintained in culture in large numbers, and they can be efficiently transformed by standard electoporation techniques. Following electroporation, transformed ES cell clones are isolated by use of positive selection for a marker gene within the DNA targeting molecule. Prior to use in production of transgenic animals, the selected ES cell clones are analyzed for the presence of disrupted PrP genes. ES cells from a clone found to have a disrupted PrP gene are injected into cultured blastocysts. Following implantation of the blastocysts in utero, the ES cells become part of the embryo and give rise to chimeric animals. In the chimeric animals, only the body tissues derived from the transgenic ES cells are transgenic. However, transgenic germ cells transmit the transgene to offspring according to normal hereditary principles.

Fusion with bacterial protoplasts, calcium-phosphate-mediated transfection, and DEAE-Dextran-mediated transfection have been used to introduce foreign DNA into mammalian cells. Although those methods may be used in the present invention, they are not preferred.

Production of Transgenic Birds

Transgenic chickens have been produced (Salter et al., *Virology,* 157, pp. 236–40 (1987); Bosselman et al., *Science* 243, 533–35 (1989); European Patent Publication 0424044A1). However, avian anatomy and physiology make manipulation and culturing of the early embryo impractical. Therefore, techniques such as direct microinjection of the pronucleus of individual cells, or electroporation of ES cells, which are preferred for mammalian systems, are not suited to avian systems. For practice of the present invention on avian systems, the method of Bosselman et al., described below, is preferred.

Even though the embryo of newly-laid fertile bird egg has undergone significant development, it is still pluripotent. Injection of a modified avian leukosis virus bearing the foreign DNA ("transgene") into the yolk near the embryo results in infection of embryonic cells and integration of the transgene into the genome of those cells. The resulting birds (generation "G-0") are chimeric, and carry the transgene in their germ cells at a useful frequency. Genetic screening of the G-0 birds followed by conventional animal breeding and progeny testing are then applied to obtain birds homozygous for the transgene. The preferred method for production of transgenic birds lacking PrP genes comprises:

(1) inserting the DNA targeting fragment into an avian retrovirus-derived vector by conventional recombinant DNA techniques, (2) injecting the targeting fragment-bearing retrovirus into the yolk of a newly laid fertile egg, near the embryo, (3) screening newly hatched chicks (G-0) for integrated proviral/targeting fragment DNA (eg., by a dot-blot procedure), (4) mating viremic G-0 male birds selected in step (3) to specific pathogen free females, (5) screening chicks (generation "G-1") produced in step (4) for integrated proviral/targeting fragment DNA, (6) mating G-1 birds to each other, and (7) screening chicks (generation "G-2") produced in step (6) for site-specific integration of the targeting fragment (eg., by PCR techniques or Southern hybridization analysis).

The preceding discussion focusses on the differences between production of transgenic mammals and transgenic birds. It should be apparent that practice of the present invention on arian species requires a suitable cloned PrP gene for construction of the targeting fragment. Such a gene can be obtained by conventional recombinant DNA techniques, including use of published chicken PrP protein partial amino acid sequences to synthesize oligonucleotide probes for screening an avian DNA library. Another method of obtaining an avian PrP gene involves screening an avian DNA library with a fragment of a previously cloned mammalian PrP gene. One of skill in the art will also recognize that since no antibiotic resistance marker is involved in the method described above for production of a transgenic bird, the disrupting sequence inserted into the cloned PrP gene during construction of the targeting molecule need not be an antibiotic resistance gene.

In view of the above, it should be apparent that the practice of this invention is not limited to a particular animal species, a particular pluripotent cell type for transformation by the foreign DNA, or a particular technique for introducing foreign DNA into the pluripotent cell. One of skill in the art will readily select cell culture and DNA delivery systems appropriate to the animal species.

The mouse is a convenient model system for the present invention. In addition to the obvious economies in feeding and maintenance that accompany the use of a small mammal species, the large litter size and short gestation period are important considerations for rapid progress on the invention. Furthermore, experimental transmission of scrapie to mice and hamsters (Chandler, *Lancet* 1, pp. 1378–79 (1961); Zlotnik and Rennie, *J. Comp. Pathol.* 75, pp. 147–57 (1965)) has provided a valuable laboratory model for determining the nature of the infectious agent and studying the disease. While the Examples set forth below recite experiments performed on mice, for the foregoing reasons, the gene transfer technology necessary for the practice of this invention has already been extended to commercially important livestock such a sheep, goats, pigs and cattle (Pursel et al. *Science* 244, pp. 1281–88).

In order that the invention described herein may be more fully understood, the following examples are set forth. It should be understood that these examples are for illustrative purposes only and are not to be construed as limiting this invention in any manner. Throughout these examples, all molecular cloning reactions were carried out according to methods in T. Maniatis et al., *Molecular Cloning: A Laboratory Manual*, Cold Spring Harbor Laboratory (1982) or J. Sambrook et al., *Molecular Cloning—A Laboratory Manual, 2nd Ed.*, Cold Spring Harbor Press (1989), using commercially available enzymes except where otherwise noted.

EXAMPLE 1

Construction Of Targeted DNA Molecules For Disrupting Prion Encoding Sequences By Homologous Recombination We constructed targeting vector pRVPrP-3 (FIGS. 1–5) by replacing codons 4 to 187 of the 254-codon PrP open reading frame (552 bp extending from nucleotide 10 to 562), with a 1.1 kb fragment containing the HSV TK promoter followed by a neomycin phosphotransferase ("neo") gene. The neo gene confers resistance to neomycin, kanamycin and G418 (Genecitin®). DNA starting materials consisted of the Westaway cosmid (a gift from David Westaway) (described below), plasmid pBluescript, a commercially available mammalian expression plasmid (see Short et al., *Nuc. Acids Res.* 16, p. 7583 (1988); product literature from Strategene Cloning Systems) and pMC1neoPA, a commercially available neomycin resistance plasmid (see Thomas and Capecchi, *Cell,* 51, pp. 503–12 (1987); product literature from Strategene Cloning Systems).

Figure 2:
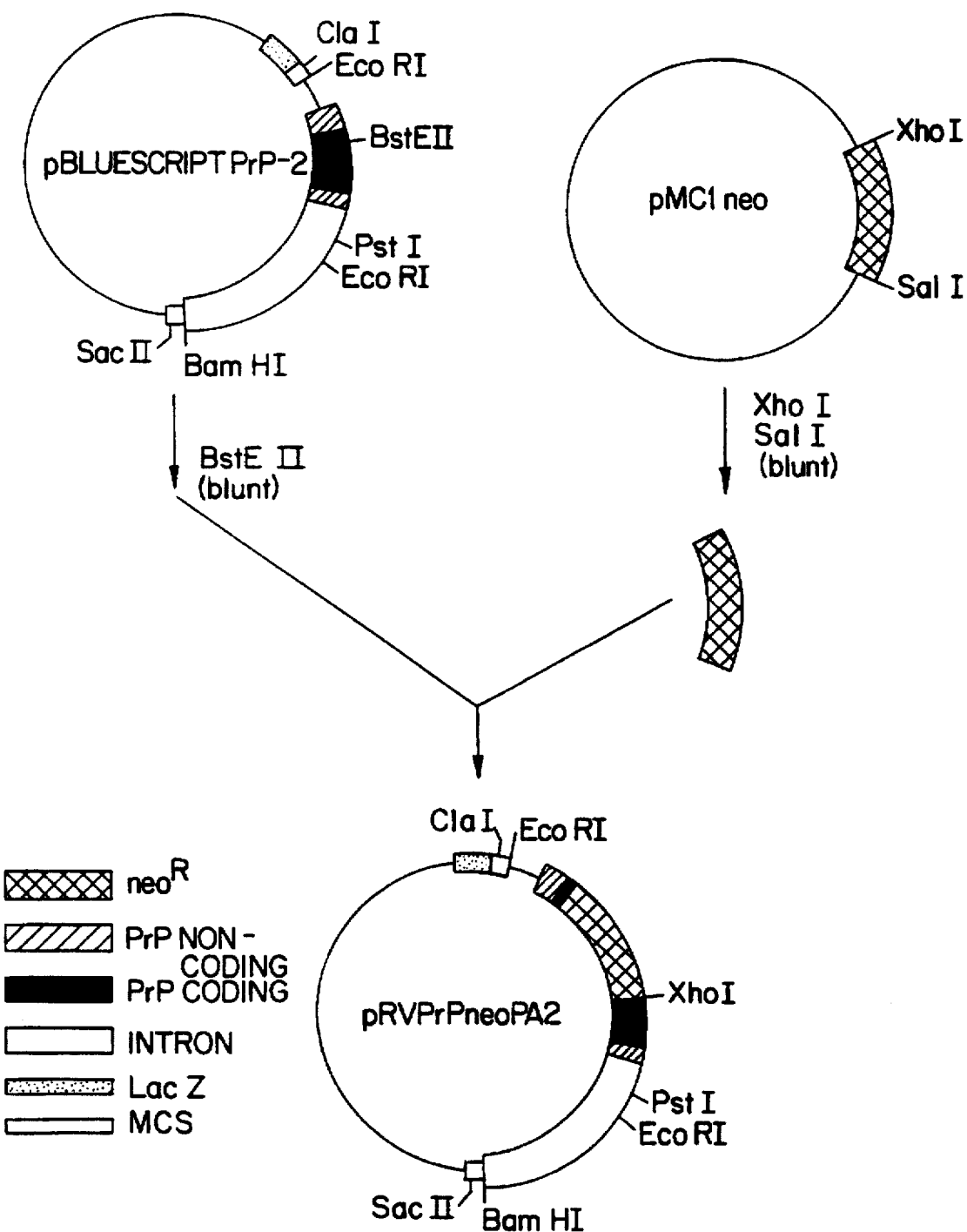
FIG. 2 depicts construction of plasmid pRVPrPneoPA2 from plasmids pBluescriptPrP-2 and pMC1neo.

The Westaway cosmid consists of (BamHI and EcoRI-cleaved) pUC18 (see product literature from GIBCO-BRL, Gaithersburg, Md.; Yanisch-Perron et al., *Gene* 33, p. 103 (1985)) with an 8.9 kb BamHI—BamHI mouse genomic insert containing Prn-p exon 3 (which encodes the entire prion protein) and part of the adjacent intron. We subcloned a 4.2 kb BamHI-EcoRI fragment containing exon 3 and the partial intron into the (BamHI and EcoRI-cleaved multiple cloning site ("MCS") of pBluescript to produce a first intermediate plasmid, pBluescriptPrP2 (FIG. 1). We excised the neo gene and its expression control sequences ("neoPA expression cassette") from pMC1neo with XhoI and SalI and inserted it by blunt-end ligation at the BstEII site (near codon 187) of exon 3, to produce a second intermediate plasmid, pRVPrPneoPA2 (FIG. 2).

Figure 3:
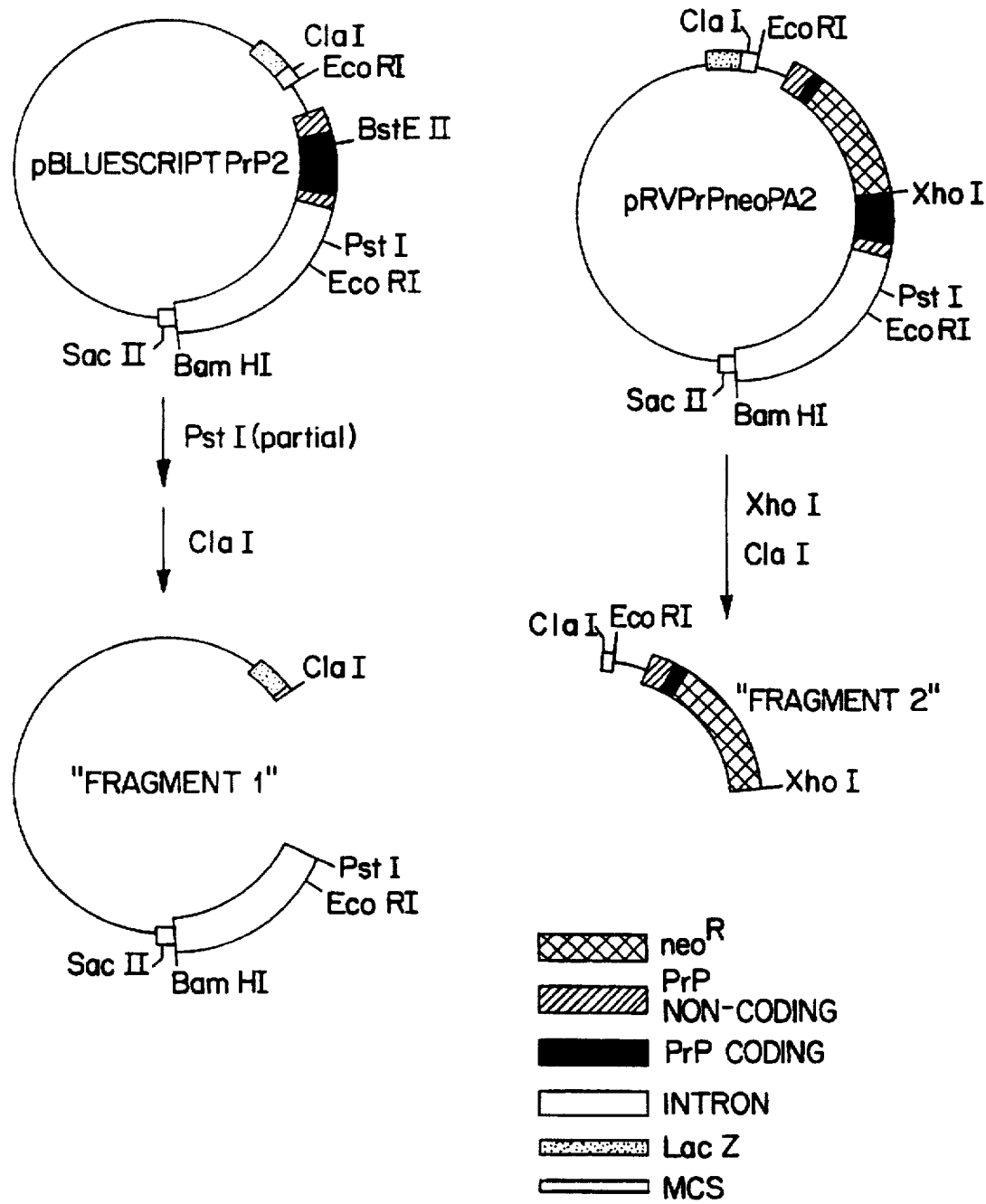
FIG. 3 depicts construction of "fragment 1" and "fragment 2" used to construct the targeting plasmid pRVPrP3.
Figure 4:
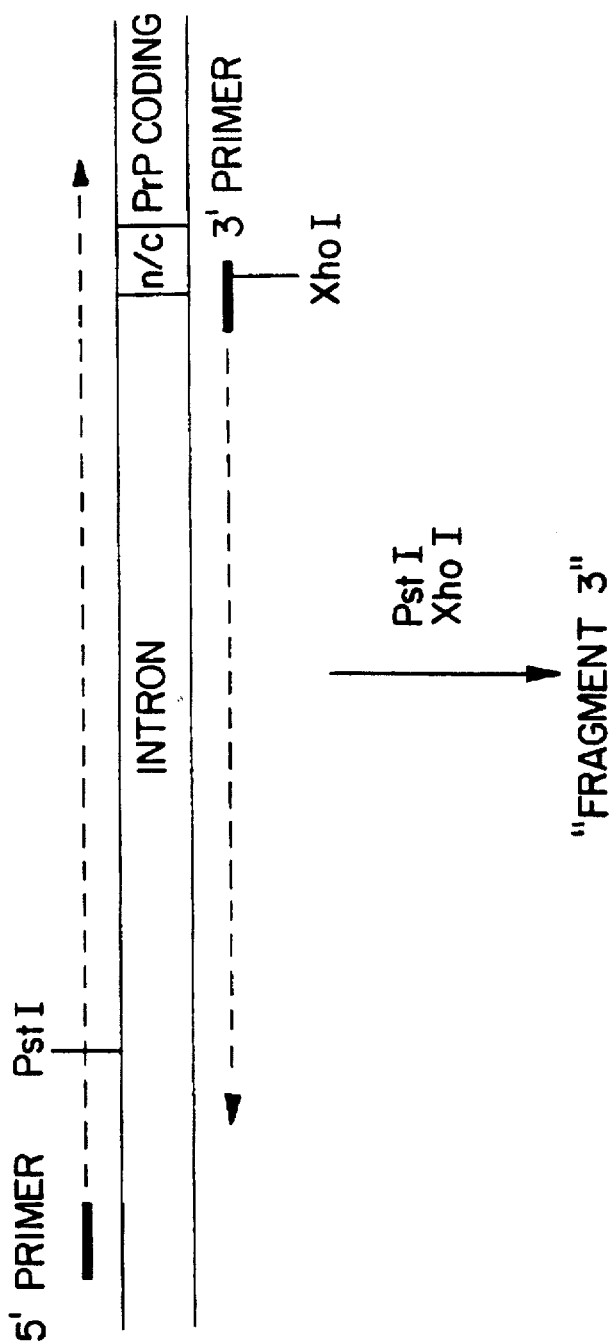
FIG. 4 depicts the synthesis of "Fragment 3" by the polymerase chain reaction ("PCR") method, using linearized pBluescript-PrP2 as the template. "Fragment 3" is used to construct the targeting plasmid pRVPrP3.
Figure 5:
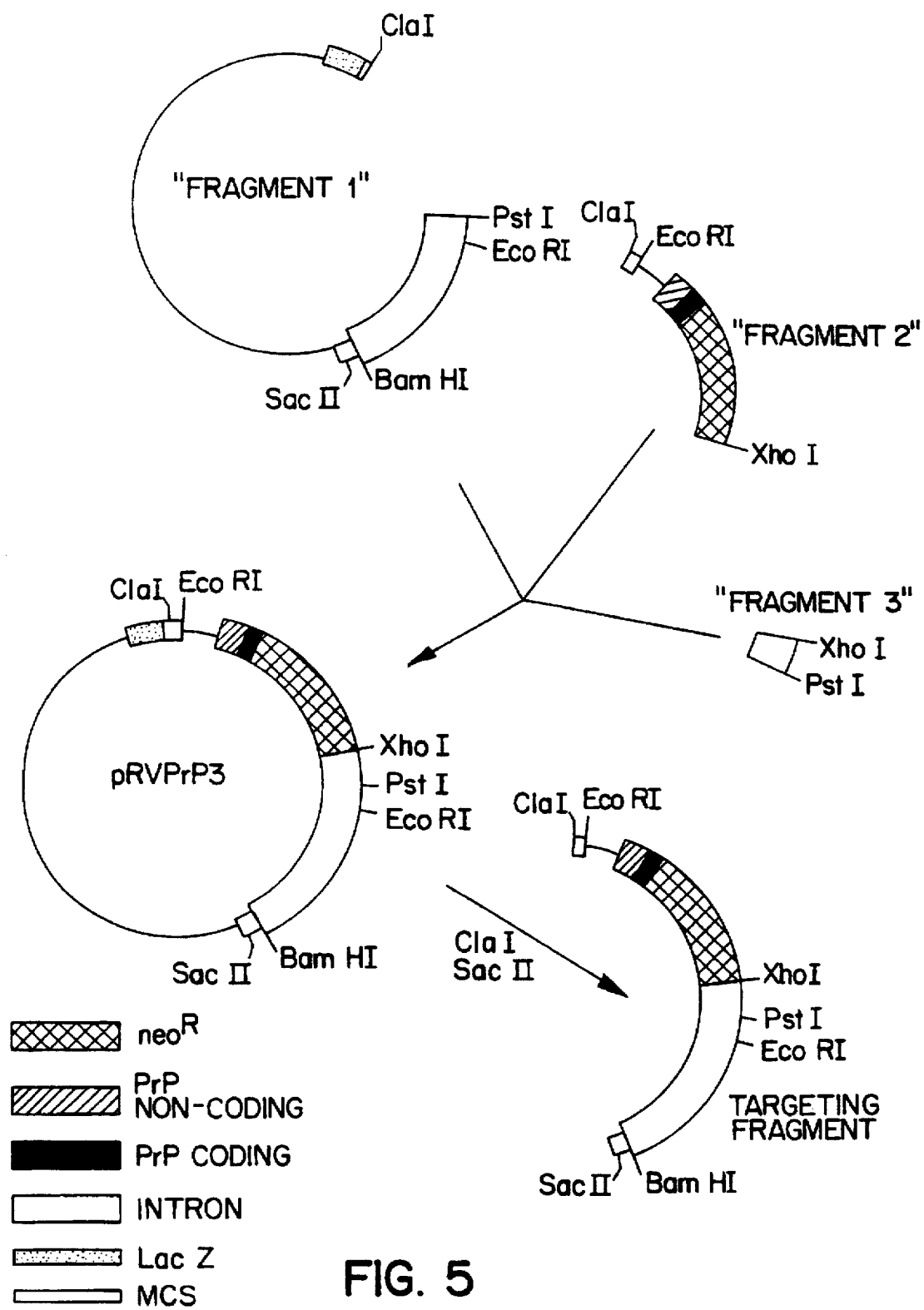
FIG. 5 depicts construction of the targeting plasmid from fragments 1–3, and excision of the targeting fragment from the targeting plasmid.

The final step in constructing targeting plasmid, pRVPrP3, involved ligation of 3 fragments (FIG. 5). "Fragment 1", the 5.5 kb PstI-ClaI fragment of pBluescriptPrP2, contains the Bluescript vector and PrP intron sequence between the BamHI site and the PstI site (FIG. 3). "Fragment 2", the 1.7 kb XhoI-ClaI fragment of pRVPrPneoPA-2 contains the neoPA expression cassette followed by the remaining PrP coding sequence downstream from the obliterated BstEII, non-coding sequences extending to the EcoRI site, and part of the Bluescript MCS region (FIG. 3). "Fragment 3", required to reconstruct the region between the PstI site in the intron and the XhoI site at the 5' end of the neoPA cassette, was generated by polymerase chain reaction ("PCR"), using linearized pBluescript-PrP2 as the template. The 5' terminal primer, "P5" (SEQ ID NO:1):

(5')GCTTTCTTCAAGTCCTTGCT CCTGCTGTAG(3'), is complementary to intron sequences upstream of the PstI site. The 3' terminal primer, "PrP-Xho" (SEQ ID NO:2):

(5')TGACTCGAGG GTTCGCCATG ATGACT(3'), is complementary to the intron-exon boundary, and has an artificial XhoI site (underlined) near its 5' end. We obtained the 0.49 kb "fragment 3" by digesting the reaction product with PstI and XhoI. "Fragment 3" extends from the PstI site to position +10 (relative to the PrP initiation codon).

We isolated the 4.8 kb ClaI-SacII fragment of pRVPrP-3, for use as a targeting fragment in transfections (FIG. 5). The targeting fragment comprises the neoPA cassette flanked at one end by the mouse intron sequence and part of the PrP 5' non-coding sequence, and at the other end, by the 3' 28% of the PrP coding sequence and the 3' non-coding region of the PrP gene.

EXAMPLE 2

Generation And Characterization OF ES Cells And Mice With Disrupted Prn-p Genes

Cell Culture and Electroporation

We cultured strain AB-1 murine embryonic stem ("ES") cells (derived from agouti sv129 mice) on irradiated G418-resistant,* leukemia inhibitory factor ("LIF")-expressing SNL76/7 feeder cells and passaged ⅙ every 2 days in DMEM 20% FCS. Both cell lines were provided by A. Bradley (McMahon and Bradley, *Cell* 62, 1073–85, (1990)).

G418 (commercially available as Genecitin®, GIBCO BRL, Gaithersburg, Md.) is a neomycin-type antibiotic to which ES cells are normally sensitive and to which the neo gene confers resistance.

We distributed about $3 \times 10^7$ trypsinized cells in 1.4 ml PBs into 2 cuvettes and electroporated with about 10 μg of purified ClaI-SacII targeting fragment described in Example 1 (above), in each cuvette. For electroporation, we used standard techniques (see generally, Chu et al., *Nuc. Acids. Res.* 15, p. 1311 (1987)) and a commercially available apparatus (BioRad Gene Pulser). Our electroporation parameters were 240 v/500 μF.

Identification of ES Cells with the Targeting Fragment Integrated by Homologous Recombination We used a 2-step selection strategy to identify ES clones with the targeting fragment integrated at the proper locus by homologous recombination. Since the targeting fragment contains the neoPA cassette, cells that integrate that fragment into a chromosome, either by random insertion or by homologous recombination, express neomycin resistance. Following electroporation, we plated the cells onto (10) 90 mm feeder plates. After 24 hours we added 0.3 mg G418/ml of medium, as the first selection step. After 10–12 days we picked G418-resistant colonies into individual wells of a 96-well plate, trypsinized them, and resuspended them. We plated aliquots of the cell suspensions onto irradiated feeder cells in 48-well master plates, and pooled the remaining cells of each well in groups of 12. We used PCR techniques (see generally, Sambrook et al., (supra), Chapter 14) to identify G418-resistant colonies with the targeting sequence integrated by homologous recombination. We lysed about 50,000 cells for each PCR analysis. Our PCR techniques were essentially as described by Saiki et al. (*Science,* 239, pp. 487–91 (1988)). We cycled 35 times for 1 min. at 94° C., and 3 min. at 70° C., with primers "P3" (SEQ ID NO:3):

(5')ATTCGCAGCG CATCGCCTTC TATCGCC(3'), which is complementary to the 3' end of the neoPA cassette, and "P4" (SEQ ID NO:4):

(5')CCTGGGAATGAACAAAGGTTTGCTTTCAAC (3'), which is complementary to PrP genomic sequences adjacent to the targeting fragment (FIG. 5). These primers give rise to an 850-bp PCR product only when the targeting fragment is integrated into the PrP locus. A positive control ES cell was generated by transforming D3 ES cells with a construct that contained additional 3' flanking sequences (the 1.3 kb EcoRI-XbaI segment shown in FIG. 1), including the primer binding site for P4, absent from the targeting vector.

After transformed murine ES cell clone ESΔP-37/10 gave positive results in the PCR screening (above), we used Southern hybridization analysis to confirm that clone ESΔP-37/10 had one Prn-p allele disrupted by the targeting fragment. Our probe in the Southern analysis was probe A, a 0.650 kb BstEII-EcoRI fragment mapping to the 3' end of the targeting fragment, which hybridizes to both endogenous and exogenous PrP sequences.

Generation of Chimeric Mice from Transformed ES Cells

We injected blastocysts from C57BL/6 (black) mice with ESΔP-37/10 cells, and implanted the blastocysts into foster mothers (genotype ICR) essentially as described by Bradley ("Production and Analysis of Chimaeric Mice", in *Teratocarcinomas and Embryonic Stem Cells: A Practical Approach,* (E. J. Robertson, ed.) Oxford IRL Press, pp. 113–51, (1987)). About 45% of the resulting offspring were partially, and 35% more than 90% chimeric in agouti coat color.

EXAMPLE 3

Transgenic Mice—Breeding And Progeny Analysis

Chimeric males were mated at age 7 weeks to C57BL/6J females. Of 22 fertile males, 9 high grade and 3 medium (20–30%) grade transmitted the agouti marker to their offspring. We determined progeny genotype by PCR analysis of tail DNA (Hogan et al., *Manipulating the Mouse Embryo*, Cold Spring Harbor Press (1986)). We used primers P10 and P4 in separate reactions to show the presence of the normal PrP allele (1.1 kb band). Primer P10 (SEQ ID NO:5):

(5')GTACCCATAA TCAGTGGAAC AAGCCCAGC(3')

hybridizes to the PrP sequences that were replaced by the neoPA cassette in the recombined allele. Samples were recycled 35 times for 1 min. at 94° C., 2 min. at 66° C., 1 min. at 70° C. We confirmed PCR genotype results by Southern hybridization analysis. For Southern analysis, we blotted and hybridized XbaI-cleaved DNA with either probe A (see above) or a probe encompassing the neoPA sequence, derived from pMC1neoPA (Stratagene).

Screening of 147 agouti offspring showed about 50% to be heterozygous for the disrupted Prn-p allele. Southern hybridization analysis confirmed the presence of the disrupted gene ("Prn-p$^{0/+}$"). Only a single copy of the targeting sequence had been integrated into the mouse genome, as shown by the fact that a probe specific for the neo gene hybridized only a single XbaI fragment of the expected length, 4 kb. Because the targeting sequence contained only a single XbaI site, each integration event should yield additional fragments of 4.8 or 5.4 kb, depending on their orientation relative to each other.

Mating of Prn-p$^{0/+}$ heterozygotes yielded 103 superficially indistinguishable progeny. PCR analysis of the DNA of the 103 progeny revealed that 23% were homozygous for the wild type PrP gene, 52% were heterozygous, and 25% were homozygous for the disrupted PrP gene. Southern hybridization analysis confirmed the genotype of the homozygous Prn-p$^{0/0}$ mice. The average life span of these homozygotes has not yet been determined, but no spontaneous deaths occurred up to 13 weeks.

EXAMPLE 4

Analysis Of Brain Tissue Of Homozygous Prn-p$^{0/0}$ Mice

Northern analysis of Prn-p$^{0/0}$ mice revealed no detectable amount of full-length PrP mRNA. However, as expected, we detected a neo-PrP fusion transcript by using a neo probe or probe A. Similarly, Western analysis of brain extracts from Prn-p$^{0/0}$ mice, using anti-PrP polyclonal antibodies revealed no detectable prion protein.

EXAMPLE 5

Gross Anatomy Of Homozygous Prn-p$^{0/0}$ Mice

We observed no gross abnormalities in the homozygous Prn-p$^{0/0}$ mice. Brain anatomy, as judged by microscopic examination of serial sections, appeared normal. Some mice showed localized vacuolization in the hippocampus, but the incidence was similar in wild type, heterozygous Prn-p$^{0/+}$ and homozygous Prn-p$^{0/0}$ animals. Thus, the hippocampal vacuolization is unrelated to PrP gene disruption.

EXAMPLE 6

Resistance to Scrapie Infection

Mice Devoid of Prion Protein

We subjected 57 homozygous Prn-p$^{0/0}$ mice (devoid of prion protein) and 57 Prn-p$^{+/+}$ mice (normal controls) to scrapie inoculation. We inoculated the mice of both groups intracerebrally with a high dose (about 10$^7$ infectious units) of the Chandler strain of mouse-adapted prions. We sacrificed 4 animals from each group after 4 days, and after 2, 8, 12 and 20 weeks. From each sacrificed animal, we recovered the brain and spleen for infectivity determination. We also subjected the brain to histological examination.

The normal control mice showed scrapie symptoms at 158±11 days, and they died at 171±11 days. The mice devoid of prion protein appeared healthy 252 days after inoculation, which was 49 days after the last Prn-p$^{+/+}$ controls died.

The infectivity time-course experiment revealed that brain extracts from control mice, at 12 weeks after inoculation, gave rise to disease in CD-1 indicator mice after 140 days. In the corresponding tests with brain or spleen extracts from mice devoid of prion protein, no detectable transmission of scrapie occurred.

The above results show that mice devoid of prion protein are completely protected against spongiform encephalopathy. The above results also indicate that mice devoid of prion protein cannot propagate scrapie.

Mice With Reduced Levels of Prion Protein

Heterozygous Prn-p$^{0/+}$ mice have only one gene encoding prion protein, rather than two. Such heterozygotes produce prion protein, but at a lowered level, due to a gene dosage effect.

To test for scrapie resistance resulting from a lower-than-normal (but non-zero) prion protein level, we inoculated a Prn-p$^{0/+}$ heterozygote intracerebrally with about 10$^7$ infectious units of the Chandler strain of mouse-adapted prions. The heterozygous mouse appeared healthy 260 days after inoculation. In a similar scrapie resistance test involving a group of heterozygous Prn-p$^{0/+}$ mice, the heterozygous mice appeared healthy at 150 days after inoculation.

The demonstration that Prn-p$^{0/+}$ heterozygous mice are much more resistant to scrapie than a wild-type (i.e., Prn-p$^{+/+}$) mice indicates that even a moderate reduction of prion protein synthesis confers at least partial protection against spongiform encephalopathy.

EXAMPLE 7

Gene Complementation Tests

To conclusively demonstrate that the observed resistance to scrapie infection and transmission was caused by the absence of prion protein, we re-introduced prion genes into our transgenic Prn-p$^{0/0}$ mouse strain and tested for restoration of scrapie susceptibility. In this experiment, we used tgHaPrn-p mice. The tgHaPrn-p strain (produced by Stanley Prusiner et al.) is homozygous for a chromosome bearing 30–50 copies of the Syrian hamster Prn-p gene. The tgHaPrn-p mouse strain is highly susceptible to hamster prions and somewhat less susceptible to mouse prions than wild type (Prn-p$^{+/+}$) mice. We mated Prn-p$^{0/0}$ mice with tgHaPrn-p mice and identified Prn-p$^{0/+}$/HaPrn-p$^{0/+}$ progeny. We backcrossed those progeny with Prn-p$^{0/0}$ mice and identified Prn-p$^{0/0}$/HaPrn-p$^{0/+}$ individuals. We inoculated (as described above) groups of 9–11 Prn-p$^{0/0}$/HaPrn-p$^{0/+}$ mice with Chandler strain mouse scrapie prions or Sc237 strain hamster prions. The mice inoculated with hamster prion strain Sc237 showed neurological symptoms after 56±3 days, and died after 59±5 days. As of 140 days after inoculation, the mice that received the mouse prions were without disease symptoms.

We claim:

1. A transgenic mouse homozygous for endogenous prion gene disruption, said disruption resulting from insertion of a selectable marker gene sequence or other heterologous sequences into the genome by homologous recombination, wherein said disruption prevents expression of functional endogenous prion protein, and, wherein lack of expression of endogenous prion protein renders said mouse unsusceptible to prion diseases and replication of the infectious agent.

2. A DNA targeting molecule capable of specifically functionally disrupting expression of an endogenous gene encoding prion protein in mammalian cells wherein disruption of said prion-encoding gene occurs by homologous recombination.

3. The DNA targeting molecule of claim 2 wherein the targeting molecule is the 4.8 kb ClaI-SacII fragment of the pRVPrP3 plasmid.

4. A mammalian cell transformed with a DNA targeting molecule according to claim 2, wherein the DNA targeting molecule has functionally disrupted one or more of the endogenous prion protein-encoding genes, wherein the cell is selected from the group consisting of ES cells and cells from cultured cell lines, and, wherein said disruption prevents expression of functional endogenous prion protein from said gene.

5. The mammalian cell of claim 4 wherein the targeting molecule is the 4.8 kb ClaI-SacII fragment of the pRVPrP3 plasmid.

6. A method of disrupting expression of functional endogenous prion protein in a mammalian cell comprising the step of disrupting one or more endogenous genes encoding prion proteins by homologous recombination with a DNA targeting molecule specific for the gene and capable of specifically functionally disrupting expression of said endogenous gene.

7. The method of claim 6 wherein the targeting molecule is the 4.8 kb ClaI-SacII fragment of the pRVPrP3 plasmid.

* * * * *